(12) United States Patent
Yang

(10) Patent No.: US 12,622,610 B2
(45) Date of Patent: May 12, 2026

(54) HIGHLY INTEGRATED ANALYTE DETECTION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 711 days.

(21) Appl. No.: 18/015,535

(22) PCT Filed: Jul. 8, 2021

(86) PCT No.: PCT/CN2021/105107
§ 371 (c)(1),
(2) Date: Jan. 11, 2023

(87) PCT Pub. No.: WO2022/012400
PCT Pub. Date: Jan. 20, 2022

(65) Prior Publication Data
US 2023/0255517 A1 Aug. 17, 2023

(30) Foreign Application Priority Data

Jul. 15, 2020 (WO) ................ PCT/CN2020/102017

(51) Int. Cl.
*A61B 5/1455* (2006.01)
*A61B 5/00* (2006.01)
(Continued)

(52) U.S. Cl.
CPC ........ *A61B 5/14532* (2013.01); *A61B 5/0002* (2013.01); *A61B 5/002* (2013.01);
(Continued)

(58) Field of Classification Search
CPC .................................................. A61B 5/1455
See application file for complete search history.

(56) References Cited

U.S. PATENT DOCUMENTS

| | | | | |
|---|---|---|---|---|
| 8,862,197 B2 * | 10/2014 | Kamath | ............. | A61B 5/14542 |
| | | | | 600/347 |
| 2009/0069650 A1 * | 3/2009 | Jennewine | .......... | A61M 5/1723 |
| | | | | 600/309 |
| 2024/0389895 A1 * | 11/2024 | Yang | .................... | A61B 5/7264 |

FOREIGN PATENT DOCUMENTS

| | | |
|---|---|---|
| CN | 110296970 | 10/2019 |
| CN | 110621227 | 12/2019 |

(Continued)

OTHER PUBLICATIONS

"International Search Report (Form PCT/ISA/210) of PCT/CN2021/105107," mailed on Sep. 28, 2021, pp. 1-2.

*Primary Examiner* — Marjan Fardanesh
(74) *Attorney, Agent, or Firm* — JCIP GLOBAL INC.

(57) ABSTRACT

A highly integrated analyte detection device is provided. The transmitter is composed of a shell, a cover body, a circuit module and an electrical connection module. The circuit module is fixedly connected with the shell, one end of the electric connection module is fixedly connected with the circuit module, the other end extends to the outside through the through hole on the shell, and is electrically connected with other structural parts. The sealing material is filled between the electric connection module and the through hole, and the cover body and the shell are clamped together to form a seal for the circuit module, which makes the transmitter structure simpler. The shell and the circuit module can be processed separately and then assembled. The production process is less difficult and the production cost is reduced at the same time.

11 Claims, 8 Drawing Sheets

(51) Int. Cl.

| | |
|---|---|
| *A61B 5/145* | (2006.01) |
| *A61B 5/1468* | (2006.01) |
| *A61B 5/1473* | (2006.01) |
| *A61M 5/158* | (2006.01) |
| *A61M 5/172* | (2006.01) |
| *B01L 3/00* | (2006.01) |
| *H01M 50/247* | (2021.01) |
| *H01M 50/271* | (2021.01) |

(52) U.S. Cl.

CPC ........ *A61B 5/14503* (2013.01); *A61B 5/1451* (2013.01); *A61B 5/14546* (2013.01); *A61B 5/1468* (2013.01); *A61B 5/1473* (2013.01); *A61B 5/683* (2013.01); *A61B 5/6838* (2013.01); *A61B 5/6848* (2013.01); *A61B 5/6849* (2013.01); *A61M 5/158* (2013.01); *A61M 5/1723* (2013.01); *B01L 3/502715* (2013.01); *B01L 3/505* (2013.01); *B01L 3/508* (2013.01); *H01M 50/247* (2021.01); *H01M 50/271* (2021.01); *A61B 2560/0214* (2013.01); *A61B 2560/045* (2013.01); *A61B 2560/0462* (2013.01); *A61B 2560/0468* (2013.01); *A61B 2562/16* (2013.01); *A61B 2562/225* (2013.01); *A61B 2562/227* (2013.01); *A61M 2205/0216* (2013.01); *A61M 2205/0233* (2013.01); *B01L 2200/0689* (2013.01); *B01L 2300/023* (2013.01); *B01L 2300/0609* (2013.01); *B01L 2300/0645* (2013.01); *B01L 2300/0663* (2013.01); *B01L 2300/123* (2013.01); *B01L 2400/0677* (2013.01)

(56) References Cited

FOREIGN PATENT DOCUMENTS

| | | |
|---|---|---|
| CN | 111093472 | 5/2020 |
| CN | 211014024 | 7/2020 |
| JP | 2019103785 | 6/2019 |

* cited by examiner

102

1022

1023

10211

10212

1021

HIGHLY INTEGRATED ANALYTE DETECTION DEVICE

CROSS-REFERENCE TO RELATED APPLICATION

This application is a 371 of international application of PCT application serial no. PCT/CN2021/105107, filed on Jul. 8, 2021, which claims the priority benefit of PCT application no. PCT/CN2020/102017, filed on Jul. 15, 2020. The entirety of each of the above-mentioned patent applications is hereby incorporated by reference herein and made a part of this specification.

TECHNICAL FIELD

The invention mainly relates to the field of medical devices, in particular to a highly integrated analyte detection device.

BACKGROUND

The pancreas in a normal human body can automatically monitor the level of glucose in the human blood and automatically secrete the required insulin/glucagon. In diabetics, the pancreas does not function properly and cannot produce the insulin the body needs. Therefore, diabetes is a metabolic disease caused by abnormal pancreatic function, and diabetes is a lifelong disease. At present, there is no cure for diabetes with medical technology. The occurrence and development of diabetes and its complications can only be controlled by stabilizing blood glucose.

Diabetics need to have their blood glucose measured before they inject insulin into the body. At present, most of the testing methods can continuously measure blood glucose and send the data to a remote device in real time for the user to view. This method is called Continuous Glucose Monitoring (CGM). The method requires the device to be attached to the skin and the probe it carries is inserted into the tissue fluid beneath the skin.

The transmitter of analyte detection device should not only form good waterproof and insulation protection for the circuit, but also make effective and reliable electrical connection between the circuit and the structural parts (such as sensors) outside the transmitter. However, the transmitter shell of existing analyte detection devices on the market adopts the integral packaging process, and the transmitter shell is molded around the circuit and the metal contacts as a whole, so as to fix the metal contacts on the circuit and form waterproof and insulating protection for the circuit at the same time. This kind of production and processing technology is relatively complicated and expensive.

Therefore, the existing technology urgently needs a transmitter structure, simple production and processing technology of highly integrated analyte detection device.

BRIEF SUMMARY OF THE INVENTION

The invention implementation case exposes a highly integrated analyte detection device, circuit module is fixed in the transmitter casing, electrical connection module connected to the circuit module is fixed at one end, and the other end through hole of the shell and external electrical connections, hole filling sealing material between the module and electrical connections, the lid of the transmitter, shell and sealing material on the circuit module form the waterproofing, insulation, sealing, at the same time, the sealing material plays a fixed role in the electric connection module, which strengthens the connection reliability between the electric connection module and the circuit module. The transmitter structure and the production and processing technology are simple, and the cost of the analyte detection device is low.

The invention discloses a highly integrated analyte detection device, which comprises a base, which is used for mounting on the surface of human skin; The sensor, the sensor is assembled on the base, the sensor comprises a signal output end and a detection end, the signal output end is provided with at least two first electrical connection area; Transmitter, transmitter including shell, the cover body, a circuit module and electrical connection module, card cover body and the shell, shell and pan card, shell also includes at least one hole, fixed connection circuit module and shell, one end of the electric connection module with fixed connection circuit module, the other end extends outwards through a through-hole in the housing, filling sealing material between hole and electric connection module; The electrical connection module includes at least two second electrical connection areas, the second electrical connection area is electrically connected with the first electrical connection area; A connecting piece, the connecting piece comprises at least two conductive areas and an insulating area, the conductive area and the insulating area arranged alternately; And the battery, which is used to power the transmitter.

According to one aspect of the invention, the electrical connection module and the circuit module are fixed by solder.

According to one aspect of the invention, the solder is solder paste.

According to one aspect of the invention an electrical connection module is connected to a circuit module by a wire.

According to one aspect of the invention, the sealing material is one or more combinations of elastic material, insulating material or waterproof material.

According to one aspect of the invention, the sealing material is one of epoxy resin, silica gel, silicone resin or polyurethane resin.

According to one aspect of the invention, the volume resistivity of the sealing material is $10^{10} \sim 10^{15}$ $\Omega \cdot$cm.

According to one aspect of the invention, the housing also includes a concave section whose contour corresponds to the sensor contour and in which the sensor is located when the second electrical connection section is electrically connected to the first electrical connection section.

According to one aspect of the invention, the other end of the electrically connected module is projected on the surface of the sealing material.

According to one aspect of the invention, the sealing material surrounds the electrical connection module.

According to one aspect of the invention, the connector is an elastic material.

According to one aspect of the invention, a second electrical connection area is projected on the surface of the sealing material.

Compared with the prior art, the technical scheme of the invention has the following advantages:

The invention discloses a highly integrated analyte detection device, the transmitter consists of shell, the cover body, circuit and electric connection module, shell and cover the body's close connection, open a hole on the shell, removable fixed connection circuit module and shell, the electric connection module end fixed on the circuit module, the other end of the through hole is connected with external structure electricity. Sealing materials are filled between the through hole and the electrically connected module, so the shell, the cover body, the circuit module and the electrically connected module can be processed and manufactured at the same time, and then assembled after the finished products are obtained respectively, which reduces the production process difficulty and cost, and at the same time, the analyte detection device transmitter with simple structure and good sealing performance can be obtained.

Further, the electric connection module and the circuit module are connected by solder, the processing technology is simple, in order to ensure that the electric connection module and the circuit module have good electrical contact at the same time, but also can make the electric connection module reliably fixed on the circuit module.

Further, the electric connection module can also be connected with the circuit module through the wire. The placement position of the electric connection module can have more choices, which is also convenient for the circuit design of the circuit module.

Further, sealing material for epoxy resin, silicone, silicone resin and polyurethane resin with waterproof and insulation properties of elastic material, can be filled in the hole and the small micro between the electric connection module, the function of sealing at the same time, also can avoid the current crosstalk between different electric connection area, guarantee the reliability of the analyte detection data, it also prevents water droplets from entering the transmitter housing, which facilitates the use of detection devices in wet and underwater environments and enhances the user experience.

Further, the transmitter and the sensor are equipped with a connector that plays the role of conduction and insulation at the same time, which reduces the complexity of the internal structure of the detection device, makes the internal structure of the detection device more compact and improves the integration of the detection device.

Further, the circuit module is fixed on the shell by means of glue or clamping. The production process is simple and the cost is low.

Further, the transmitter shell also includes a concave part, whose contour corresponds to the sensor contour, and when the second electrical connection area is electrically connected with the first electrical connection area, the sensor is located in the concave part, which can reduce the overall thickness of the transmitter and the base.

Further, the other end of the electric connection module is protruded on the surface of the sealing material, which facilitates the electric connection between the electric connection module and the external structural parts of the transmitter, and ensures the reliability of the electric connection between the transmitter and the external structural parts.

Further, the connector is made of elastic material, and the elastic connector will be deformed by extrusion, which can obtain better electrical contact and also play a cushioning role.

4

Figure 4A:
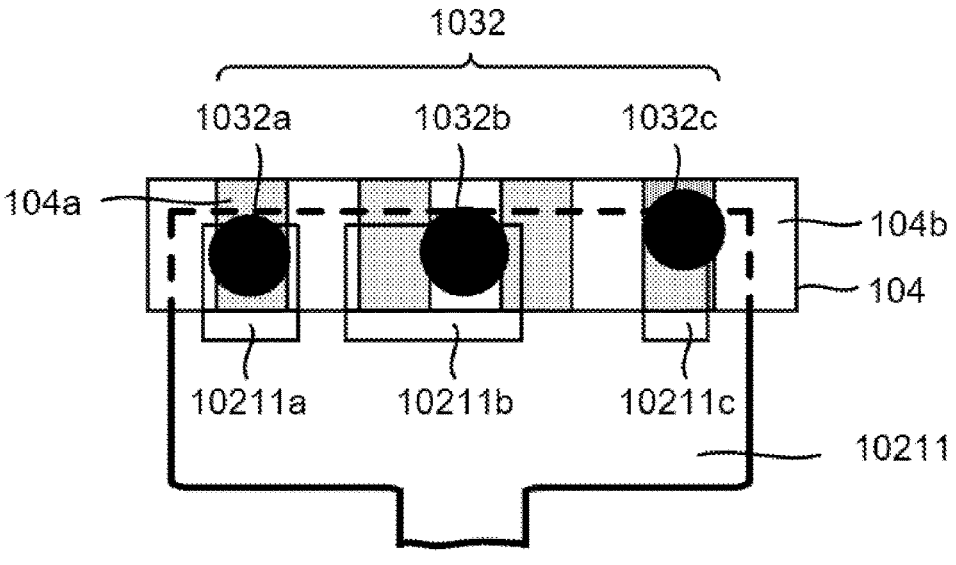
Figure 4B:
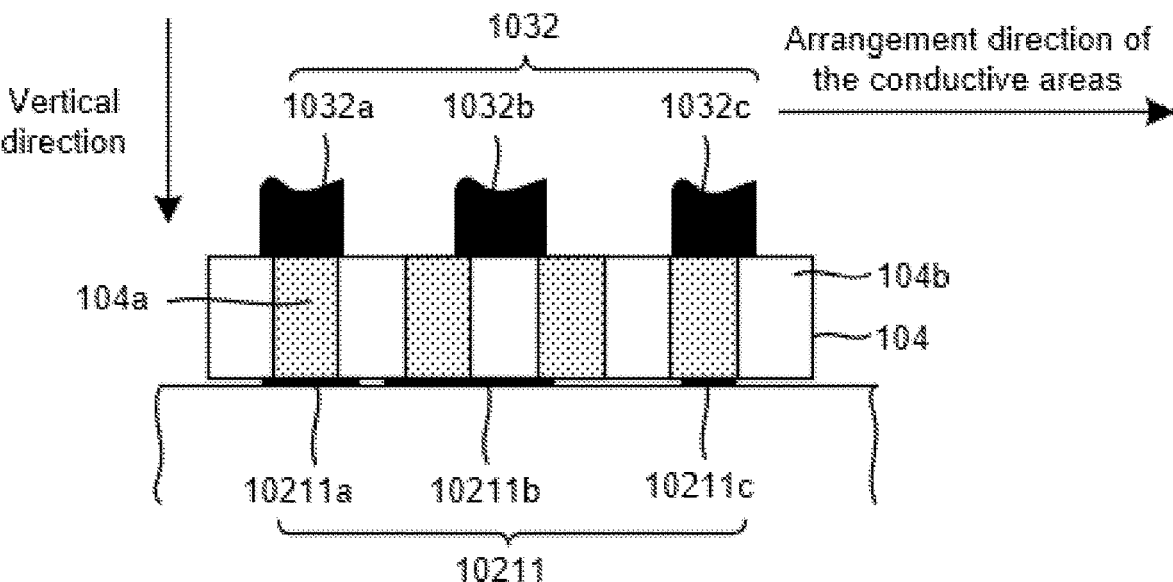
Figure 4C:
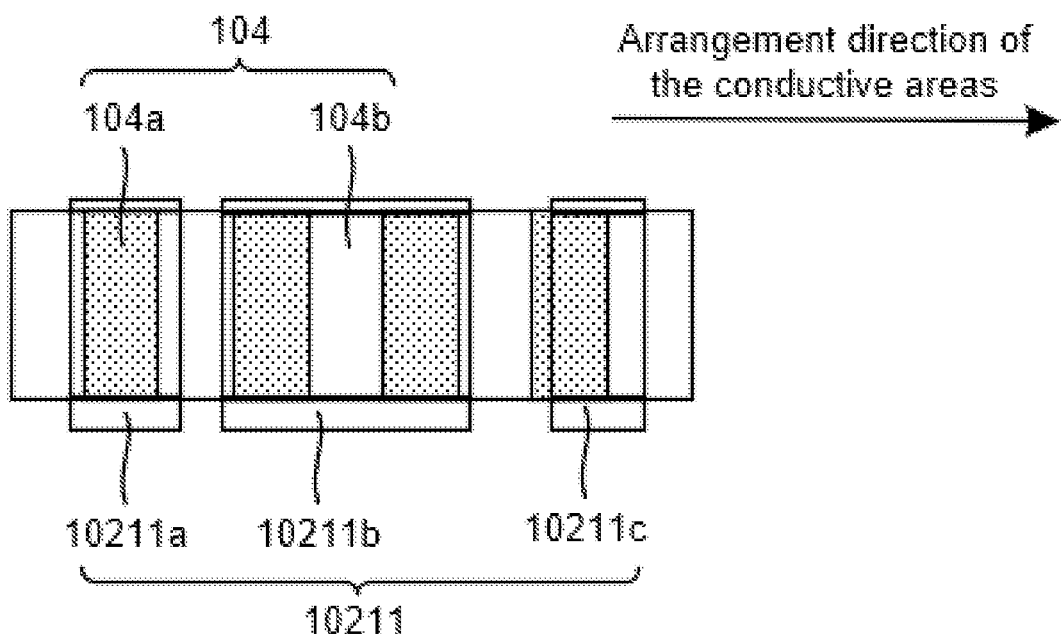
Figure 4D:
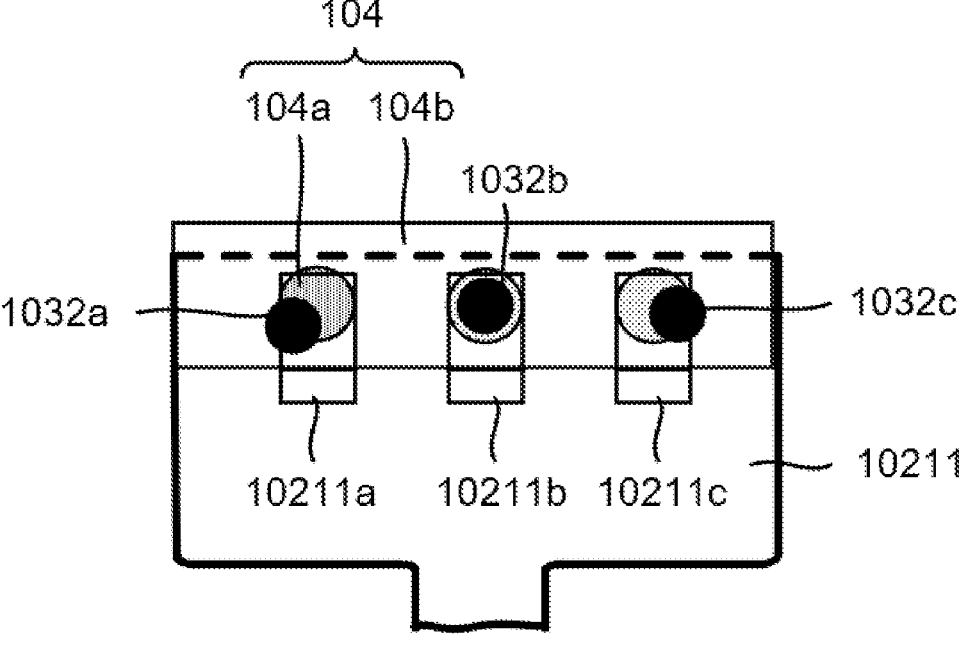
Figure 4E:
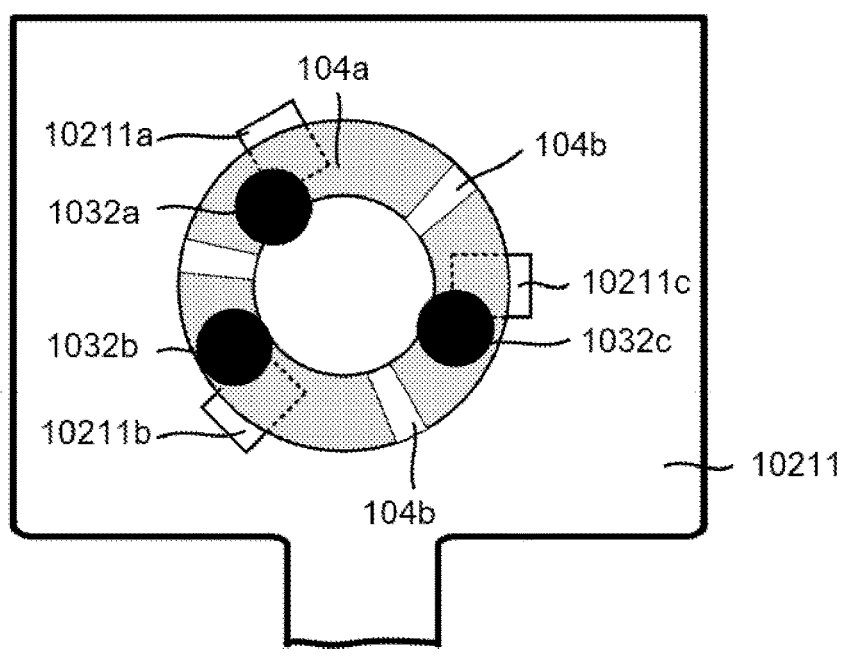
Figure 5:
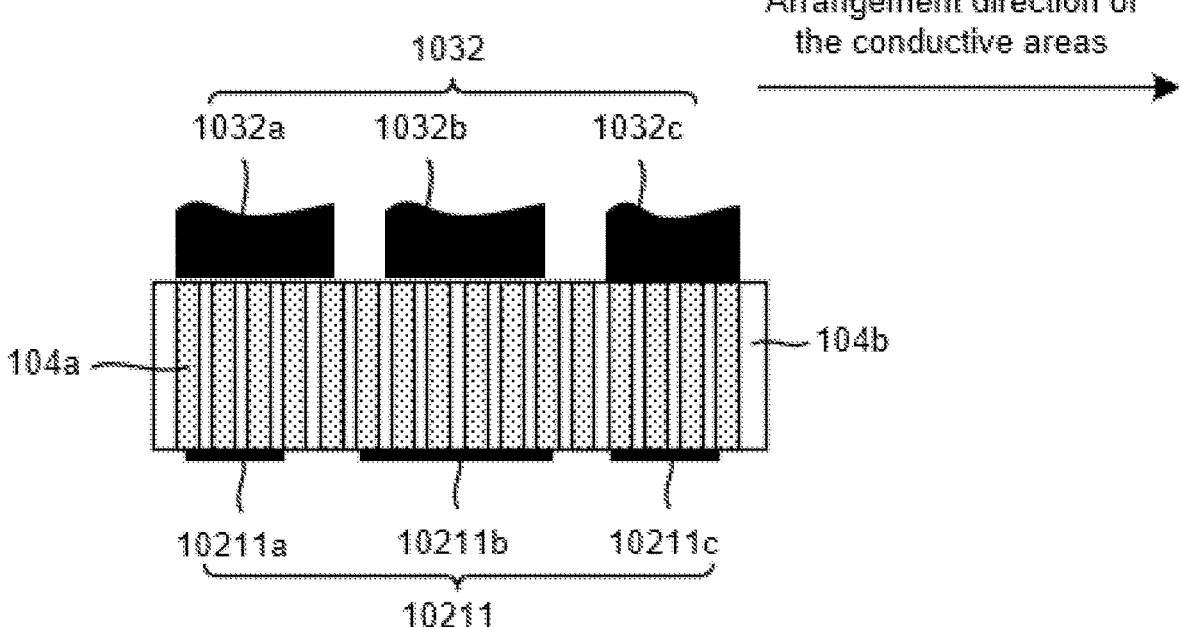
Figure 6:
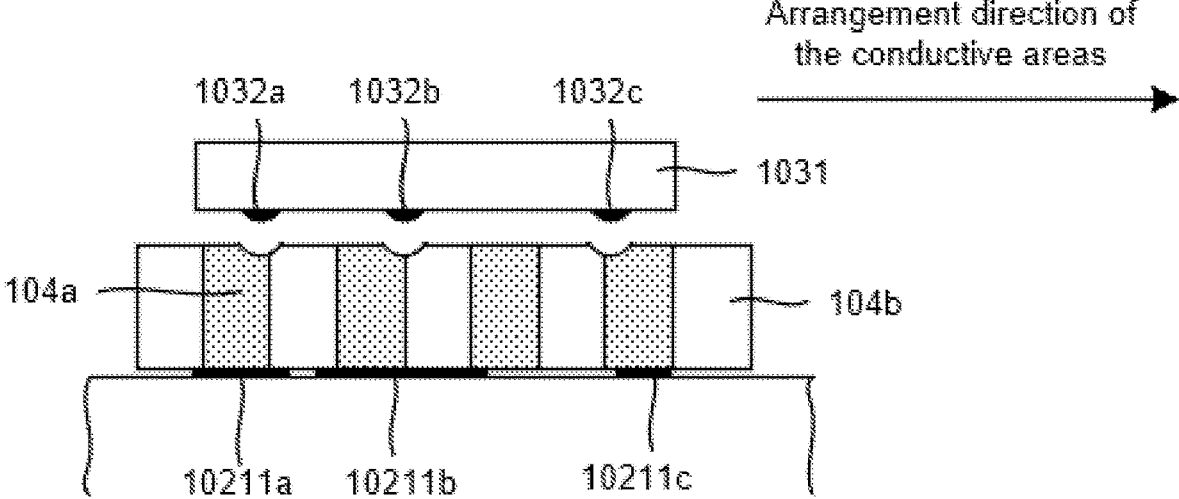
Figure 7A:
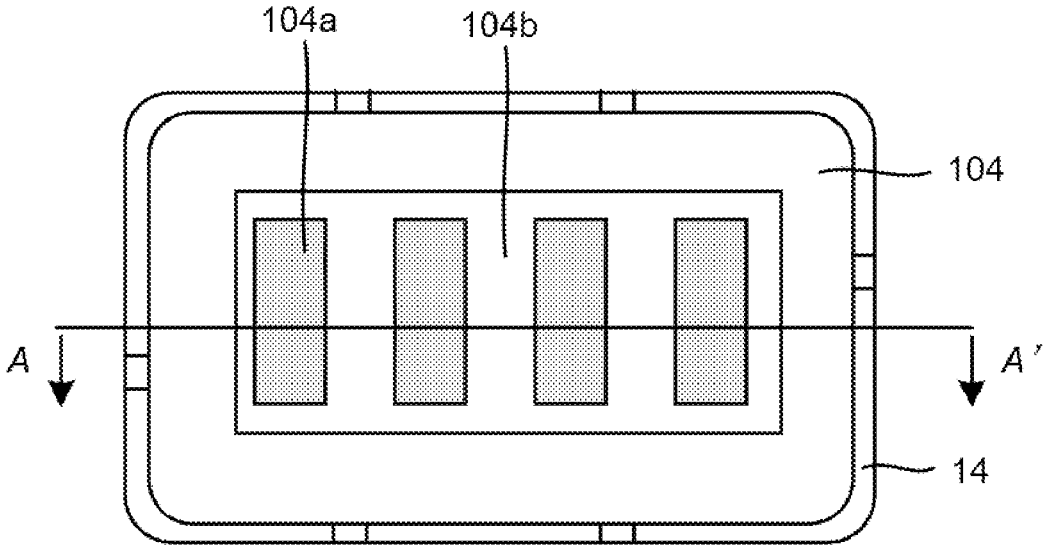
Figure 7B:
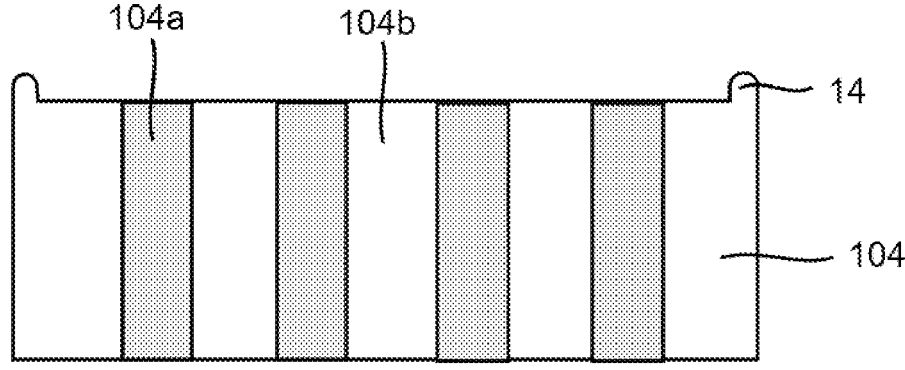

FIG. 4a is a schematic diagram of the overhead structure of the connector, the first electrical connection area and the second electrical connection area according to the embodiment of the invention;

FIG. 4b is a side view of the connector in FIG. 4a;

FIG. 4c is a schematic diagram of the overhead structure of the first electrical connection area according to another embodiment of the invention;

FIG. 4d-FIG. 4e is a schematic diagram of the overhead structure of the connectors, the first electrical connection area and the second electrical connection area according to different embodiments of the invention;

FIG. 5 is a structural schematic diagram of a connector, a first electrical connection area and a second electrical connection area according to another embodiment of the invention;

FIG. 6 is a structural schematic diagram of the second electrical connection area and the electrical connection position of the connector according to another embodiment of the invention;

FIG. 7a-FIG. 7b is A structural schematic diagram of another embodiment of the invention in which an elastic connector is simultaneously used as a seal, and FIG. 7b is a cross-section diagram of an elastic connector obtained along section lines a-a' in FIG. 7a.

DETAILED DESCRIPTION

As mentioned above, the transmitter structure and production process of the analyte detection device are complex and the production cost is high. It is found that the cause of the problem for existing transmitters in the production of detection devices, around the circuit module and electrical connection module for overall injection molding processing, to seal on the formation circuit and electric connection module, the production process is difficult, get transmitter structure is more complex, increased the cost of production.

In order to solve the problem, the present invention provides a highly integrated analyte detection device, the transmitter by the shell, the cover body, a circuit module and the electrical connection modules, fixed connection circuit module and shell, the electric connection module connected to the circuit module is fixed at one end, the other end extends outwards through a through-hole in the housing, and other structures electrical connections, the sealing material is filled between the electric connection module and the through hole, and the cover body and the shell are clamped together to form a seal for the circuit module, which makes the transmitter structure simpler. The shell and the circuit module can be processed separately and then assembled. The production process is less difficult and the production cost is reduced at the same time.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e.g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this Manual.

It should be noted that similar labels and letters indicate similar items in the appending drawings below, so that once an item is defined or described in one of the appending drawings, there is no need to discuss it further in the subsequent appending drawings.

Figure 1:
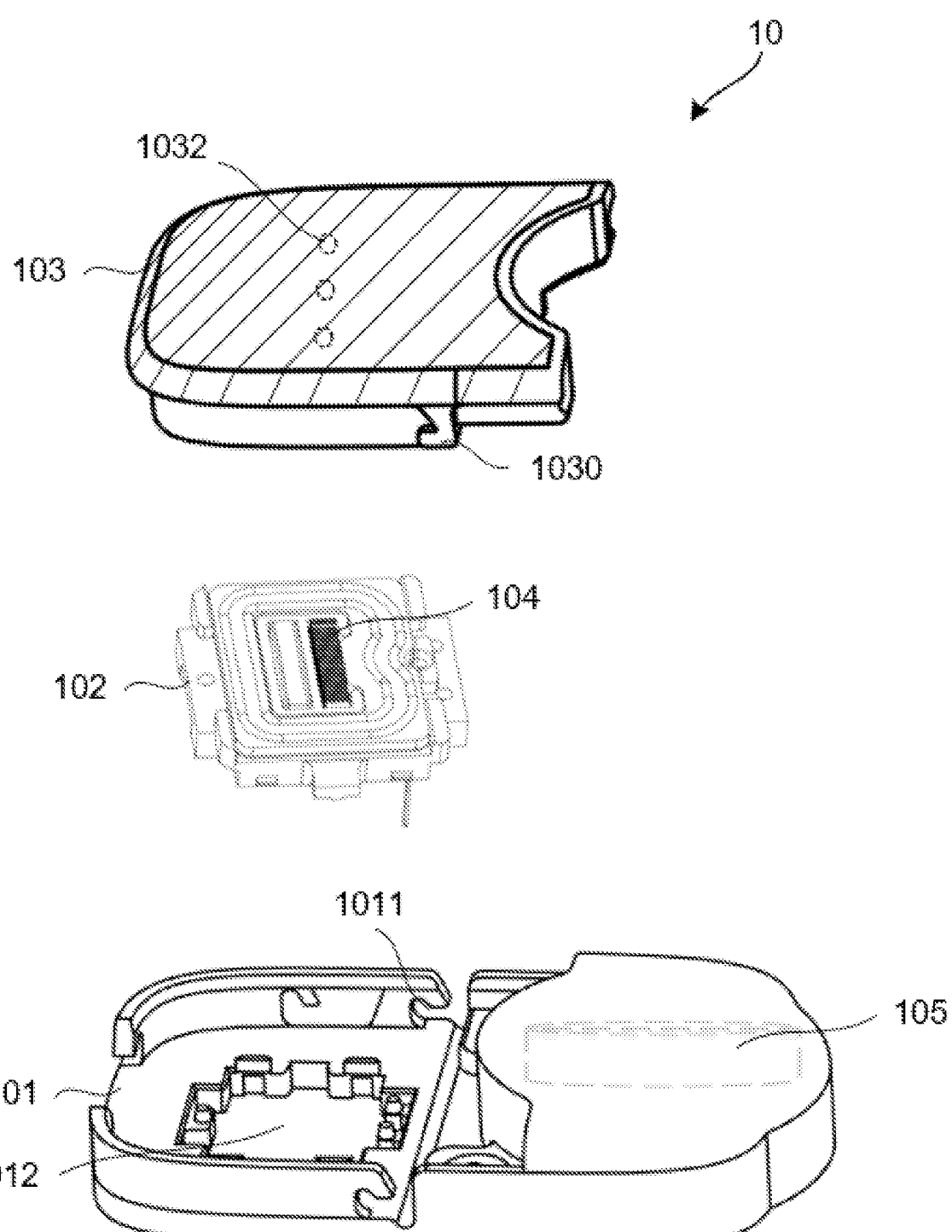
FIG. 1 is a schematic diagram of the three-dimensional structure of a high-integration analyte detection device according to an embodiment of the invention.

FIG. 1 is a schematic diagram of the three-dimensional structure of a highly integrated analyte detection device according to an embodiment of the invention. The highly integrated analyte detection device 10 includes chassis 101, sensor 102, transmitter 103, connecting piece 104 and battery 105. A first clamping part 1011 for fixing the transmitter 103 is arranged on the side wall of the chassis 101, and a second clamping part 1030 corresponding to the first clamping part 1011 is arranged on the side wall of the transmitter. The first clamping part 1011 and the second clamping part 1030 are clamped together to fix the transmitter 103 and the chassis 101. An assembly hole 1012 for auxiliary installation of sensor 102 is also provided on the chassis 101. The shape of the assembly hole 1012 is consistent with the edge shape of sensor 102 to assist the installation of sensor 102 on the chassis 101. The battery 105 is also sealed on the chassis 101. When the transmitter 103 is clamped on the chassis 101, the battery 105 is used to provide power for the transmitter 103.

In other embodiments of the present invention, the battery 105 is enclosed within the transmitter 103 for providing electrical energy to the transmitter 103.

In another embodiment of the present invention, the chassis 101 may also be of other shapes. For example, the chassis 101 only has a side wall for attachment to the sensor 102, and a clamping part for fixing the transmitter 103 is provided on the bottom surface. The transmitter 103 is installed on the chassis 101 by sliding or other means.

In other embodiments of the present invention, other shape choices may be made for the chassis 101, provided that the conditions for the transmitter 103 and sensor 102 to be mounted on the chassis 101 are satisfied, and no specific restrictions are made here.

Figure 2:
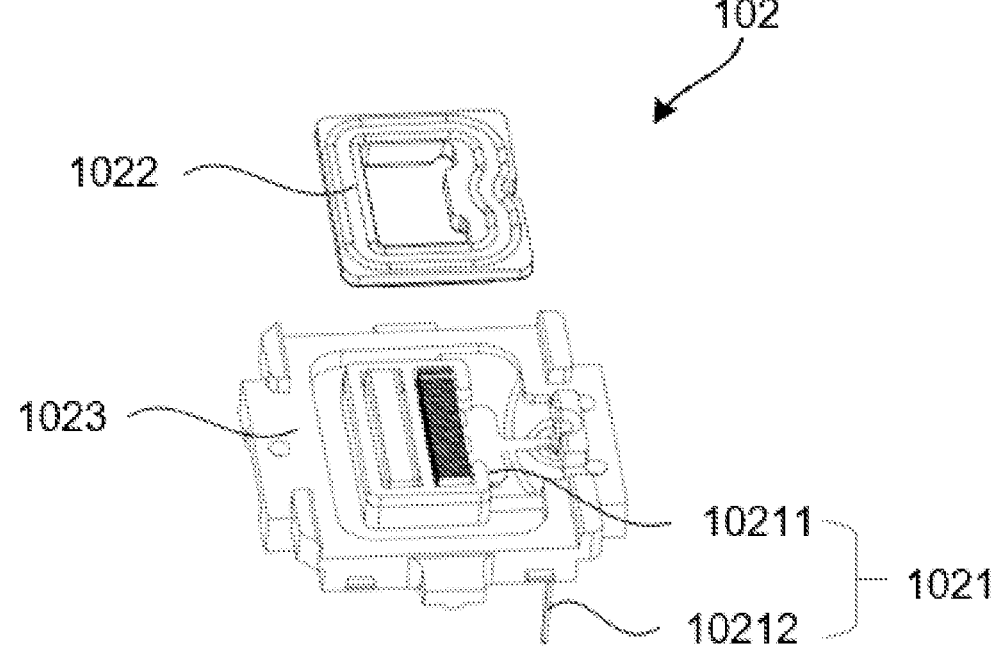
FIG. 2 is a structural schematic diagram of a sensor according to an embodiment of the invention.

With reference to FIG. 1 and FIG. 2, FIG. 2 is the structural schematic diagram of the sensor. Sensor 102 includes a signal output terminal 10211 and a detection terminal 10212. The signal output terminal 10211 is laid on the surface of sensor 102, or embedded in the sensor base. The detection terminal 10212 is bent toward the chassis 101 and is at an angle α (not shown in the figure) with the signal output terminal 10211, preferably α=90°, this design reduces the height of the sensor 102 protruding from the chassis 101 and reduces the thickness dimension of the detection device.

In other embodiments of the present invention, the sensor 113 may also be of other shapes or forms (e.g. non-bent), and no specific restrictions are made here.

There are a number of ways in which sensor 102 can be mounted on chassis 101. No specific restrictions are made here. Specifically, in the embodiment of the invention, the sensor 102 is installed on the chassis 101 through the sensor base 1023.

In another embodiment of the present invention, the auxiliary mounting structure of sensor 102 is removed after the sensor 102 is installed on the chassis 101, and the sensor 102 is not carried by the sensor base 1023 or other components, but is mounted on the chassis 101 alone. For example, the sensor 102 is mounted on one side of the chassis 101 and is attached to the side wall of the chassis 101.

In other embodiments of the present invention, sensor 102 may also be mounted to the chassis 101 in other modes of assembly, and no specific restrictions are made here.

Please continue to refer to FIG. 2, the signal output terminal 10211 is provided with a first electrical connection area (the first electrical connection area is also indicated by code 10211 below), corresponding to the second electrical connection area 1032 of transmitter 103, and connected with the second electrical connection area 1032 to transmit the detection signal to transmitter 103. The detection terminal 10212 is used to pierce human subcutaneous tissue to detect fluid analyte parameter information. Typically, sensor 102 is also provided with an electrode and/or electrode conductor (not shown here or below) for detecting analyte parameter information. The detection signal of the electrode needs to be exported through the first electrical connection area of the signal output terminal 10211.

In this case, the corresponding refers to the same number of the two, the two positions are basically corresponding. It is obvious that in the embodiment of the invention, the number of the second electrical connection area 1032 is three, corresponding to the three-electrode system of sensor 102.

In the embodiment of the invention, the second electrical connection area 1032 is exposed and protrudes on the transmitter housing 1031 for electrical contact with the first electrical connection area of the corresponding signal output terminal 10211. Specifically, in the embodiment of the invention, the second electrical connection area 1032 is a metal contact. Smaller metal contacts make the internal structure of the detection device more compact, and the volume of the detection device will be further reduced.

It is noted that embodiments of the present invention do not restrict the shape or position of the second electrical connection area 1032 or the position relationship between the second electrical connection area 1032 and the transmitter housing 1031. As in one embodiment of the invention, a second electrical connection area is arranged on one side of the transmitter. Therefore, the electrical connection position between the connector and the first electrical connection area and the second electrical connection area is located on one side of the detection device. In another embodiment of the present invention, the cross-section of the second electrical connection area 1032 is rectangular or circular.

Embodiments of the present invention do not limit the setting mode of the first electrical connection area on the signal output terminal 10211. For example, the first electrical connection area can be arranged on the surface of the signal output terminal 10211, or embedded in the signal output terminal 10211.

Generally, sensor 102 is provided with at least two detection electrodes, that is, at least including a working electrode and a counter electrode. Therefore, in the implementation of the present invention, at least two first electrical connection areas are provided on the surface of the signal output terminal 10211 for electrical connection with different electrodes. Specifically, in the embodiment of the invention, sensor 102 is a three-electrode system. Therefore, the number of the first electrical connection area is three.

Figure 3:
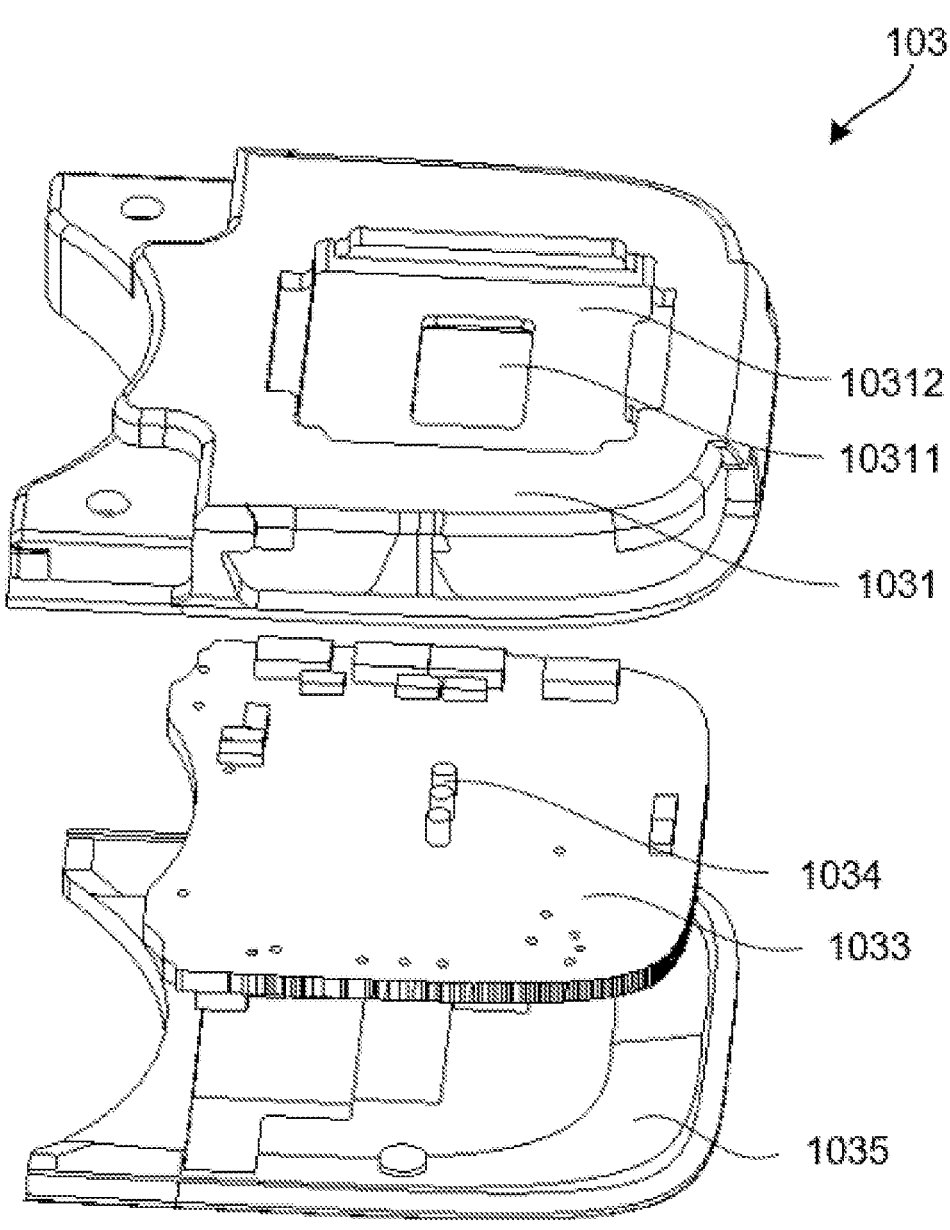
FIG. 3 is an explosion structure drawing of an transmitter in accordance with an embodiment of the invention.

In another embodiment of the present invention, sensor 102 also includes a sealing ring 1022, which surrounds the signal output 10211 and is used to provide watertight protection for the signal output 10211 and a second electrical connection area 1032 in wet or underwater environments. In the embodiment of the invention, the sealing ring material is preferred to be insulating rubber. As the rubber is a flexible material and has certain compressive elasticity, when the transmitter 103 is installed on the chassis 101, there is a certain extrusion pressure on the sealing ring 1022, which can better maintain the close contact between the sealing ring 1022 and the transmitter 103 and prevent water droplets from entering the electrical connection area. Avoid short circuit and current intensity disturbance. Combined with FIG. 1 and FIG. 3, FIG. 3 shows the explosion structure of the launcher. The transmitter 103 comprises a housing 1031, a circuit module 1033, an electrical connection module 1034 and a cover body 1035.

In the embodiment of the invention, the circuit module 1033 is fixedly connected with the transmitter shell 1031. Here, the "fixedly connected" can refer to the glue fixation, the clamping clamping fixation, or any other fixed connection mode, which can realize that the relative position of the circuit module 1033 and the transmitter shell 1031 does not change, and no specific restrictions are made here.

In the embodiment of the invention, one end of the electric connection module 1034 is welded to the circuit module 1033 through solder, which is a conductive material, so as to realize the electric connection and fixation between the electric connection module 1034 and the circuit module 1033. Preferred, solder is solder paste, solder paste is made of solder powder, flux and other surfactants, thixotropy agent to be mixed, the formation of paste mixture, at room temperature has a certain viscosity, can be electrical connection module 1034 initially stick in a fixed position, at welding temperature, with the solvent and some additives volatilization, weld the electric connection module 1034 and the circuit module 1033 together to form a fixed connection.

In other embodiments of the present invention, one end of the electric connection module 1034 is connected with the circuit module 1033 through a wire, and the electric connection module is fixed on the transmitter shell 1031. As the wire is a flexible component, the relative position of the electric connection module 1034 and the circuit module 1033 can be changed at will. According to the structural design requirements of the detection device 10, the electric connection module 1034 can be placed more choices, convenient for the device structure and circuit design.

Continuing to refer to FIG. 1 and FIG. 3, the transmitter shell 1031 is provided with at least one through hole 10311, and the other end of the electric connection module 1034 extends to the exterior of the transmitter shell 1031 through the through hole 10311, forming a second electric connection area 1032, which contacts with the first electric connection area 10211 and forms an electric connection. In the embodiment of the invention, the through hole 10311 is a rectangle, and the envelope of the electric connection module 1034 is in the middle, and the rectangular through hole is convenient for processing.

In other embodiments of the invention, the through-hole 10311 can be processed according to or not according to the contour of the electrically connected module 1034, provided that the electrically connected module 1034 can pass through the through-hole smoothly, and no specific restrictions are made here.

In order to seal the circuit module 1033 inside the transmitter 103, it is necessary to fill the sealing material (not shown in the figure) between the electrically connected module 1034 and the through hole 10311. Specifically, after the circuit module 1033 is fixed on the transmitter shell 1031 and the electric connection module 1034 is fixed on the circuit module 1033, the electric connection module 1034 is fixed on the relative position of the through hole 10311. At this time, the sealing material is filled in the tiny micro-cracks between the electric connection module 1034 and the through hole 10311. After curing, the sealing material can realize the sealing between the electric connection module 1034 and the through hole 10311. At the same time, the curing sealing material can further strengthen the fixing firmness of the electric connection module 1034 on the circuit module 1033, and increase the reliability of the electric connection.

In the embodiment of the invention, the sealing material is one or more of the elastic material, insulating material and waterproof material. The elastic property can avoid the damage caused by the sealing material to the transmitter shell 1031 where the electrically connected module 1034 and the through hole 10311 are located after curing. The insulation property can avoid the electric signal crosstalk between different electric connection modules 1034, which affects the reliability of the analyte detection system. Waterproof property can prevent water droplets from entering the transmitter shell 1031, making circuit module 1033 appear short circuit and other faults, which is convenient for users to use the analyte detection system in wet or underwater environment.

In an embodiment of the present invention, the sealing material is preferred to be polyurethane resin. The polyurethane resin has good water resistance and strong adhesion at room temperature ($23°$ C.) and is suitable for the packaging of precision components. The volume resistivity of the polyurethane resin is about $10^{14}{\sim}10^{15}$ $\Omega{\cdot}$cm, and has excellent insulation performance. It can avoid crosstalk of current signals between different electrical connection areas.

In another embodiment of the present invention, the sealing material is preferred to be epoxy resin, which has excellent adhesion at room temperature, small thermal expansion coefficient, volume resistivity of about $10^{14}{\sim}10^{15}$ $\Omega{\cdot}$cm, excellent insulation performance, and can avoid crosstalk of current signals between different electrical connection areas.

In another embodiment of the invention, the sealing material is preferred to be silica gel. In the processing process, the silica gel can be rapidly cured, and the processing efficiency is improved. The volume resistivity is about $10^{14}{\sim}10^{15}$ $\Omega{\cdot}$cm, and it has excellent insulation performance, which can avoid crosstalk of current signals between different electrical connection areas.

In this invention implementation example, sealing material for the fluid state before curing, its fluid properties can make the seal material automatically fill in electric connection module of small joint between 1034 and 10311 hole, also can form good for electric connection module 1034 surrounded, surrounded by around 1034 electric connection module, for shell 1031 form a tight seal, And keep the surface flat. In the process of filling sealing materials, it is also necessary to control the amount of sealing materials, not only to seal the transmitter shell 1031, but also to make the electric connection module 1034 protrusive on the surface of the sealing material, so that the second electric connection area 1032 of the electric connection module 1034 can form an effective electric connection with the first electric connection area 10211.

Technicians in this field can understand that the choice of sealing materials is diverse, and other types of sealing materials can be selected based on the use and needs of electronic components, not limited to the above preferred materials.

In other embodiments of the present invention, the transmitter shell 1031 also includes a concave 10312 whose contour corresponds to that of the sensor 102, where "corresponding" means that the sensor 102 can be placed just inside the concave 10312. Generally speaking, after the sensor 102 is installed on the chassis 101, the transmitter 103 is installed on the chassis 101. At this time, the sensor 102 is located in the concave 10312, so that the transmitter shell 1031 can contact the chassis 101. Thus, when the transmitter 103 is installed on the chassis 101, the overall thickness size of the transmitter and the base is reduced. The structure is more compact and easy for users to use.

Continue to refer to FIG. 3, before the circuit module 1033 is fixed on the transmitter shell 1031, the cover 1035 is separated from the transmitter shell 1031, and the cover 1035 can be fixed with the transmitter shell 1031. Here, the fixed connection refers to the detachable fixed connection or the non-detachable fixed connection, preferably the non-detachable fixed connection. In order to prevent the artificial destruction of the circuit module 1033 internal circuit and stored data, improve the reliability of detection devices.

FIG. 4a is a schematic diagram of the overhead structure of the connector, the first electrical connection area and the second electrical connection area according to the embodiment of the invention; FIG. 4b is a side view of the connector in FIG. 4a; FIG. 4c is a schematic diagram of the overhead structure of the first electrical connection area according to another embodiment of the invention; FIG. 4d-FIG. 4e is a schematic diagram of the overhead structure of the connectors, the first electrical connection area and the second electrical connection area according to different embodiments of the invention.

First of all, it should be pointed out that the thin dotted line in FIG. 4a represents the contour of the first electrical connection area covered by connectors, while the thick dotted line represents the contour of the signal output terminal covered by connectors. The fine dotted lines and thick dotted lines in the subsequent drawings have the same meaning as here, which will not be repeated below.

Connecting piece 104 is arranged between the first electrical connection area 10211 and the second electrical connection area 1032 to realize the mutual electrical connection between the two. Therefore, a conductive part must be included in connecting piece 104 to electrically connect the corresponding first electrical connection area 10211 and second electrical connection area 1032.

Connecting piece 104 comprises at least two conductive zones 104a and at least one insulating zone 104b. Conducting zone 104a and insulating zone 104b play the role of conducting and insulating, respectively. The conductive zone 104a and the insulating zone 104b cannot be separated from each other, that is, the conductive zone 104a and the insulating zone 104b belong to the integral part of the connecting piece 104 respectively.

An insulating area 104B is arranged between adjacent conductive areas 104A. Different first electrical connection area 10211 or different second electrical connection area 1032 are electrically connected with different conductive area 104a respectively, so that any two first electrical connection areas 01211 or any two second electrical connection areas 1032 are electrically insulated from each other.

Inside the connecting piece 104, the conductive zone 104a and the insulating zone 104b pass through the connecting piece 104 in the longitudinal direction, as shown in FIG. 4b. In this case, the longitudinal direction refers to the direction from the first electrical connection area 10211 to the corresponding second electrical connection area 1032, or the direction of the current between the first electrical connection area 10211 and the second electrical connection area 1032. When the first electrical connection area 10211 is electrically connected with the second electrical connection area 1032, such a design ensures that connecting piece 104 can only conduct electricity lengthways, but not horizontally. Connecting piece 104 connects the first electrical connection area 10211 with the corresponding second electrical connection area 1032, and at the same time insulates different first electrical connection areas 10211 or different second electrical connection areas 1032. A connecting piece 104 plays the role of electrical conduction and electrical insulation at the same time, the complexity of the internal structure of the detection device is reduced, the internal structure is more compact, and the integration of the detection device is improved.

It is noted that in other embodiments of the present invention, the conductive zone 104a or the insulating zone 104b may also have a certain inclination, or be arranged in other directions or ways within the connecting piece 104, without any specific restriction herein provided that the above conditions of electrical conduction and electrical insulation are satisfied.

Please refer to FIG. 2, FIG. 4A and FIG. 4B. Specifically, in the embodiment of the invention, the connecting piece 104 is a rectangular structure. The conductive zone 104a and the insulating zone 104b are separated, and the connecting member 104 is penetrated respectively. In another embodiment of the present invention, different conductive zones 104a are arranged within the same insulating zone 104b, that is, surrounded by the same insulating zone 104b, as shown in FIG. 4d. In another embodiment of the invention, the top view of connecting piece 104 may be circular, as shown in FIG. 4E. In another embodiment of the invention, the top view of connecting piece 104 may also be circular.

In other embodiments of the present invention, connection 104 may also have other shapes, provided that the conditions for the realization of the function of connection 104 are met without any specific limitation herein.

Please continue to refer to FIG. 4A and FIG. 4B. When the connecting piece 104 is electrically connected to the first electrical connection area 10211 and the second electrical connection area 1032 respectively, there is an insulation area 104b between any two first electrical connection areas 10211 connected to the connecting piece 104. Specifically, in the embodiment of the invention, the insulation zone 104b spaced between any of the above two first electrical connection zones 10211 includes a portion of an insulation zone 104b (between 10211A and 10211b in FIGS. 4a and 4b), or one insulation zone 104b, or more than one insulation zone 104b (between 10211c and 10211b in FIGS. 4a and 4b). Similarly, the insulation zone 104b separated between any two second electrical connection zones 1032 connected to connecting piece 104 includes part of one insulation zone 104b, or one insulation zone 104b, or more than one insulation zone 104b. However, it is obvious that the first electrical connection area and the corresponding second electrical connection area (such as between 10211a and 1032a, between 10211b and 1032b, or between 10211c and 1032c) share a conductive area 104a to realize the conduction of the two. The conducting region of the common part includes a portion of a conducting region 104a (between 10211c and 1032c in FIGS. 4a and 4b), or one conducting region 104a, or more than one conducting region 104a.

In combination with FIGS. 4a and 4b, it is easy for a technician in the field to understand that the above one insulating area or part of a conductive area, one insulating area or a conductive area, and more than one insulating area or a conductive area are only the span of the first or second electrical connection area in a one-dimensional direction (such as the direction in which the conductive area is distributed).

In other embodiments of the present invention, an insulating area or part of a conducting area, an insulating area or a conducting area, and more than one insulating or conducting area may also represent the coverage of the insulating or conducting area by the first or second electrical connection area in a two-dimensional direction (in area), as shown in FIG. 4c. Taking the first electrical connection area as an example, the dotted line in FIG. 4c represents part of the outline of the first electrical connection area. Obviously, the first electrical connection area 10211 can cover an insulating area or part of a conductive area, or one insulating area or a conductive area, or more than one insulating area or a conductive area.

Obviously, when the number of conductive or insulating areas between the above structures is large or the range is wide, the reliability of electrical connection or electrical insulation between the structures will be significantly improved.

In the embodiment of the invention, the connecting piece 104 is an elastic connector, and its materials include elastic plastic, elastic rubber, etc. Resilient connecting piece 104 provides better electrical contact while acting as a buffer. When the material of connecting piece 104 is elastic rubber, connecting piece 104 is conductive adhesive strip. A conductive adhesive strip plays the role of conductive and insulating at the same time, and plays the role of buffer.

Obviously, when sensor 102 is a two-electrode system, the number of the first and second electrical connection regions is both 2. At this point, connecting piece 104 only needs to include two conductive zones 104a and an insulating zone 104b arranged between the two conductive zones 104a. In other words, two pairs of different first electrical connection area and second electrical connection area are respectively connected through different conductive area 104a to realize electrical conduction. At the same time, two first electrical connection areas or two second electrical connection areas are separated by the insulation area to achieve electrical insulation.

Sensors in other embodiments of the present invention may also include additional electrodes. As a result, connecting piece 104 includes more conductive and insulating zones spaced apart from each other, providing a more flexible electrical connection, as shown in FIG. 5.

To be sure, in other cases of the present invention, the sensor includes at least three electrodes, the signal output end of the 10211 set up the first electric connection area, at least three of which at least two first electric connection area through different conductive area 104 a second electrical connection with the corresponding area electrical connection, the connection methods, in accordance with the above principle. Embodiments of the present invention do not limit the mode of connection or the principle of connection for other first and second electrical connection areas which are not connected to connection member 104. For example, in an embodiment of the present invention, the sensor is a 3-electrode system, wherein only the working electrode and the counter electrode are electrically connected to the second electrical connection area by the corresponding first electrical connection area respectively through the connector, while the reference electrode is electrically connected to the transmitter by other means.

FIG. 6 is a structural schematic diagram of the second electrical connection area and the electrical connection position of the connector according to another embodiment of the invention.

For ease of annotation and description, the second electrical connection area 1032 and connecting piece 104 in FIG. 6 will be shown separately.

As shown in FIG. 6, in an embodiment of the invention, the second electrical connection area 1032 is a bulgent spherical crown type metal contact. Accordingly, connecting piece 104 is provided with a concave portion (not shown) where it is connected to a protruding metal contact for a tighter connection. At the same time, this convex and concave connection also plays the role of fixing the position of connecting piece 104, that is, no matter what external forces the detection device is subjected to, the position of connecting piece 104 is always fixed, no displacement, to ensure that the connecting piece 104 performs normal conductive and insulating work.

It should be noted that when connecting piece 104 is an elastic connector, connecting piece 104 can be designed without concave parts. When squeezed by the protruding metal contact, the elastic connector will automatically appear a concave part matched with the metal contact to ensure the realization of electrical connection or electrical insulation function.

FIG. 7a-FIG. 7b is A structural schematic diagram of another embodiment of the invention in which an elastic connector is simultaneously used as A seal, and FIG. 7b is A cross-section diagram of an elastic connector obtained along section lines a-a' in FIG. 7a.

In order to protect the electrical connection position of the first electric connection area 10211, the second electric connection area 1032 and the connecting piece 104, the elastic connector is surrounded around the electric connection position of the first electric connection area 10211, the second electric connection area 1032 and the elastic connector respectively, so as to play the role of sealing.

Preferably, in order to better play a sealing role, a raised structure 14 is arranged around the connecting piece 104, as shown in FIG. 7a and FIG. 7b. The dotted frame in FIG. 7a indicates the distribution range of the conductive zone 104a.

In the actual manufacturing process, the thickness of each first electrical connection area will vary. When the transmitter and the sensor are connected, the independent and non-interference of the first electrical connection area can weaken or eliminate the influence of the bad contact caused by the thickness difference above, and improve the reliability of the electrical connection between the three. Preferably, when the connector is an elastic connector, the above problem of poor contact can be effectively avoided.

In the existing detection device, there are multiple separated conductive parts and/or multiple separated insulating parts between the transmitter and the sensor, and one part can only play one role, which increases the complexity of the internal structure of the detection device. At the same time, the reliability of the electrical connection between the transmitter and the sensor is poor, and the problems of signal interruption and data loss are easy to occur. In the detection device of the embodiment of the invention, the transmitter and the sensor are provided with a connector that plays the role of conducting and insulating at the same time, which reduces the complexity of the internal structure of the detection device, makes the internal structure of the detection device more compact, and improves the integration of the detection device.

The place on put together is narrated, the present invention provides a highly integrated analyte detection device, transmitters by shell, the cover body, a circuit module and the electrical connection modules, fixed connection circuit module and shell, the electric connection module connected to the circuit module is fixed at one end, on the other end through the shell pass hall to external, and other structures electrical connections, The sealing material is filled between the electric connection module and the through hole, and the cover body and the shell are clamped together to form a seal for the circuit module, which makes the transmitter structure simpler. The shell and the circuit module can be processed separately and then assembled. The production process is less difficult and the production cost is reduced at the same time.

Although some specific embodiments of the invention have been detailed through examples, technicians in the field should understand that the above examples are for illustrative purposes only and are not intended to limit the scope of the invention. Persons skilled in the field should understand that the above embodiments may be modified without departing from the scope and spirit of the present invention. The scope of the invention is limited by the attached claims.

The invention claimed is:

1. A highly integrated analyte detection device, comprising:

a base, configured to be installed on a surface of human skin;

a sensor, assembled on the base, wherein the sensor comprises a signal output end and a detection end, the signal output end is provided with at least two first electrical connection areas;

a transmitter including a shell, a cover body, a circuit module and an electrical connection module, wherein the cover body is connected to the shell, the shell comprises at least one hole, the circuit module is fixed to the shell, one end of the electric connection module is fixed to the circuit module, the other end of the electric connection module extends outwards the shell through the through-hole, the electrical connection module comprises at least two second electrical connection areas, a sealing material is filled between the through hole and the electrical connection module, when the shell is connected to the base, the second electrical connection areas are electrically connected to the first electrical connection areas;

a connecting piece, comprising at least two conductive areas and an insulating area, the conductive areas and the insulating area arranged alternately; and a battery used to provide electrical energy to the transmitter.

2. A highly integrated analyte detection device of claim 1, wherein the electrical connection module and the circuit module are fixed by solder.

3. A highly integrated analyte detection device of claim 2, wherein the solder is a solder paste.

4. A highly integrated analyte detection device of claim 1, wherein the electrical connection module is connected with the circuit module through a wire.

5. A highly integrated analyte detection device of claim 1, wherein the sealing material is at least one of an elastic material, an insulating material and a waterproof material.

6. A highly integrated analyte detection device of claim 1, wherein the sealing material is one of an epoxy resin, a silica gel, a silicone resin or a polyurethane resin.

7. A highly integrated analyte detection device of claim 1, wherein a volume resistivity of the sealing material is $10^{10} \sim 10^{15}$ $\Omega \cdot cm$.

8. A highly integrated analyte detection device of claim 1, wherein the shell also comprises a concave part, a contour of the concave part corresponds to a contour of the sensor, and the sensor is located in the concave part when the second electrical connection areas are electrically connected with the first electrical connection areas.

9. A highly integrated analyte detection device of claim 1, wherein the other end of the electric connection module is protruded from a surface of the sealing material.

10. A highly integrated analyte detection device of claim 1, wherein the sealing material surrounds the electrical connection module.

11. A highly integrated analyte detection device of claim 1, wherein the connecting piece is an elastic material.

* * * * *